United States Patent [19]

Cross et al.

[11] 3,930,403

[45] Jan. 6, 1976

[54] PISTON ASSEMBLY

[75] Inventors: William Telford Cross, Cuddington; Stephen Alexander Gaydon, Saltburn by the Sea; Andrew Gilchrist; Ernest Raymond Ellis, both of Welwyn Garden City, all of England

[73] Assignee: Imperial Chemical Industries Limited, London, England

[22] Filed: July 23, 1974

[21] Appl. No.: 491,137

[30] Foreign Application Priority Data

Aug. 8, 1973 United Kingdom............... 37588/73

[52] U.S. Cl..................................... 73/55; 417/393
[51] Int. Cl.²......................................... G01N 11/04
[58] Field of Search............................. 73/55, 56, 54

[56] References Cited
UNITED STATES PATENTS

| | | | |
|---|---|---|---|
| 2,597,138 | 5/1952 | Trigg | 73/55 X |
| 2,960,860 | 11/1960 | Viggers et al. | 73/55 |
| 3,263,494 | 8/1966 | Abbot | 73/55 |

Primary Examiner—Richard C. Queisser
Assistant Examiner—Joseph W. Roskos
Attorney, Agent, or Firm—Cushman, Darby & Cushman

[57] ABSTRACT

A transfer compressor for transmitting pressure from one fluid to another comprising a cylinder, a piston slidable within the cylinder, a space within the cylinder at each end of the piston, means for admitting fluid to each of the spaces, a tell-tale rod mounted on one end of the piston passing slidably and sealingly through an end of the cylinder, one end of the piston presenting a different area presented by the other end of the piston to the fluid in contact with said other end whereby the pressure exerted on the fluid at one end of the piston may be different from the pressure existing in the fluid at the other end of the piston.

3 Claims, 4 Drawing Figures

PISTON ASSEMBLY

This invention relates to a piston assembly and in particular to a piston assembly in which opposite ends of the piston have differing effective areas, suitable for use in a variety of high pressure applications.

In the field of high pressure technology various problems exist which are concerned with the compression, pumping, sealing and viscosity measurement of fluids maintained at high pressure. It has now been found that some of these problems may be overcome in a relatively simple manner by making use of a simple device hereinafter termed a "transfer compressor".

Accordingly there is provided a transfer compressor for transmitting pressure from one fluid to another comprising a cylinder, a piston slidable within the cylinder, a space within the cylinder at each end of the piston, means for admitting fluid to each of the spaces, a telltale rod mounted on one end of the piston passing slidably and sealingly through an end of the cylinder, one end of the piston presenting a different area to the fluid in contact with it from the area presented by the other end of the piston to the fluid in contact with said other end, whereby the pressure exerted on the fluid at one end of the piston may be different from the pressure existing in the fluid at the other end of the piston and movement of the piston within the cylinder may be detected by observation of movement of the tell-tale rod.

In order that the invention may be more clearly understood various embodiments of the invention will now be described with reference to the accompanying drawings in which.

Figure 1:
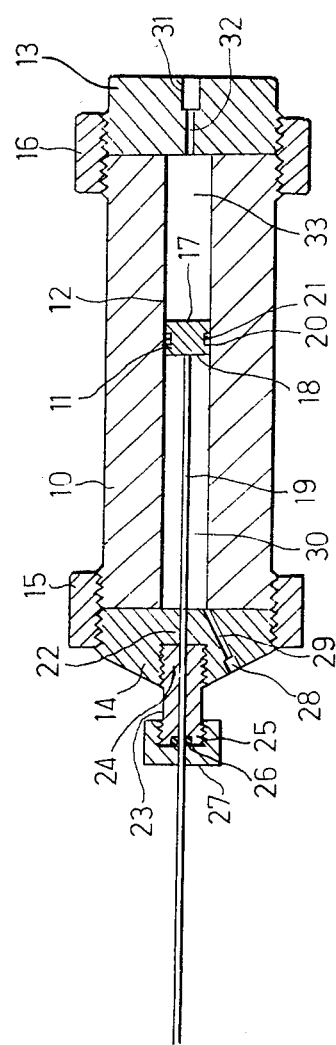
FIG. 1 is a sectional view of a transfer compressor according to the invention on a plane through an axis of the cylinder of the compressor.

The piston assembly shown in FIG. 1 consists of a thick-walled steel cylinder 10 and a piston 11 slidable within the bore 12 of the cylinder 10. The cylinder 10 is provided with closure pieces 13 and 14 which are engaged against the ends of the cylinder 10 by means of turnbuckle nuts 15 and 16. The piston 11 having ends 17 and 18 is provided with a tell-tale rod 19 attached to the end 18 and passing slidably through the closure piece 14. The piston 11 is further provided with an annular circumferential groove 20 which receives a resilient O-ring 21 to provide a slidable and sealing engagement with the bore 12.

Closure piece 14 is provided with a narrow bore 22 to slidably receive the tell-tale rod 19 and is further adapted to receive a threaded plug 23 also provided with a bore 24 to slidably receive the tell-tale rod. The threaded plug 23 is provided with a recessed portion 25 to receive a packing 26. An end-closure nut 27 adapted to slidably receive the tell-tale rod is threaded on complementary threads on the outer surface of plug 23 to secure the packing 26 and provide a slidable and sealing engagement of the tell-tale rod 19 with the end of the piston assembly.

An access port 28 is provided in closure piece 14 and is adapted to receive a connecting plug (not shown) to enable fluids to be introduced or withdrawn via a narrow bore 29 into space 30 in the end of the cylinder containing the tell-tale rod.

Closure piece 13 is provided with an access port 31 adapted to receive a connecting plug (not shown) to enable fluids to be introduced or withdrawn via a narrow bore 32 into space 33 in the end of the cylinder not containing the tell-tale rod.

In operation high pressure fluid is introduced through access port 31 into space 33 and acts on end 17 of the piston 11. The opposing force acting on end 18 of the piston 11 is determined by the pressure of the fluid contained in space 30 and the effective surface area of the end 18 of the piston, that is the area of end 18 excluding the area occupied by the attachment of the tell-tale rod 19. When the forces acting on opposite sides of the piston are equal and the piston is in force balance the fluid pressure acting in space 30 is greater than the fluid pressure acting in space 33 by an amount which is determined by the fluid pressure acting in space 30 and the ratio of the area occupied by the tell-tale rod 19 to the area of the end 17 of the piston.

By varying the cross-section of the tell-tale rod the pressure difference acting between opposite sides of the piston when it is in force balance may be varied over a wide range chosen to suit the particular application but is is preferred that this pressure difference is kept at a low level in order that complicated sealing arrangements are not required between opposite ends of the piston and for this reason the cross-sectional area of the rod relative to the cross-sectional area of the piston is preferably as small as possible. In practice the difference in pressure between opposite sides of the piston when the piston is moving will be slightly different from the static equilibrium value because of friction of the piston and tell-tale seals.

Where it is desired to vary the pressure difference acting across the piston this may be achieved without altering the relative cross-sectional areas of the piston and the tell-tale rod or the pressure acting within the cylinder by applying an external force to the tell-tale rod along its axis. This force may be applied in either direction to either increase or decrease the pressure difference across the piston. Preferably, the magnitude of the force is known in order that the pressure difference may be varied by a known amount.

Various modifications of the construction of the transfer compressor described are readily apparent. Thus either closure end piece may be formed integrally with the cylinder barrel. Additionally, the sealing arrangements of the piston and the tell-tale rod may be varied using any suitable sealing method know to the art.

In a further modification the end of the telltale rod projecting from the compressor may be provided with a means for rotating the piston. This modification permits the fluid contents of the cylinder to be agitated when desired.

As previously indicated the simple transfer compressor described may be advantageously used to overcome a number of problems in the field of high pressure technology. For example it is well known that the viscosity of fluids is extremely dependent on the pressures to which the fluids are subjected. A knowledge of the flow behaviour of fluids subjected to high pressure is essential when such a fluid is to be pumped at high pressure along a pipe or when the fluid is to be used to seal fine clearances for example in rotary shaft clearance seals or when used as a lubricant to support a rotating shaft in a bearing. Such information can be very simply obtained by making use of a transfer compressor of the type described with reference to FIG. 1 and a capillary tube.

According to a further embodiment of the invention there is provided a device for measuring the flow characteristics of a fluid at high pressure comprising a transfer compressor of the type hereinbefore described and a capillary tube wherein the ends of the capillary are connected to the spaces at the ends of the cylinder whereby a pressure difference generated between opposite ends of the piston by the application of pressure to the fluid contained in the end spaces of the cylinder causes the fluid to flow through the capillary at a rate which may be determined by the movement of the tell-tale rod.

Figure 2:
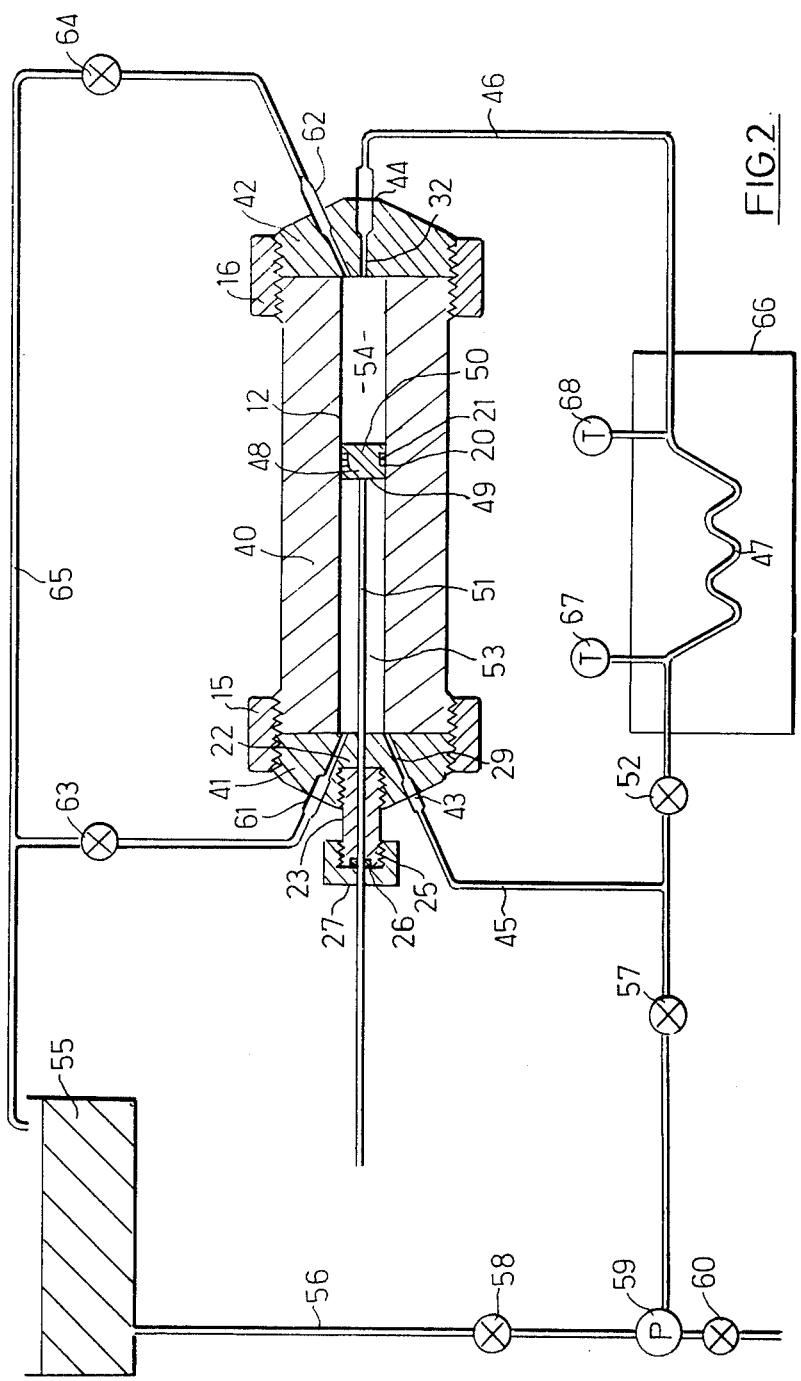
FIG. 2 is a sectional view of a transfer compressor when used together with a capillary tube to provide a means for measuring the flow characteristics of fluids at high pressure.

These measurements may be performed using an embodiment of the invention illustrated in FIG. 2 in which a transfer compressor of the type hereinbefore described is used in conjunction with a narrow bore capillary tube. A cylinder 40 of the transfer compressor is provided with end closure pieces 41 and 42 and is connected through access ports 43 and 44 by means of conduits 45 and 46 to a thick-walled capillary tube 47. The cylinder 40 is provided with a piston 48 having ends 49 and 50 and a tell-tale rod 51 connected to end 49. Conduit 45 is provided with a stop valve 52 for isolating spaces 53 and 54 on either side of the piston from each other. A reservoir 55 contains the fluid to be examined. A conduit 56 connects reservoir 55 to conduit 45 and is provided with stop valves 57 and 58, a pump 59 and a drain valve 60. Cylinder 40 is further provided with access ports 61 and 62 connected through stop valves 63 and 64 respectively to a return conduit 65 to the reservoir 55. The capillary tube 47 is surrounded by a constant temperature bath 66 and the ends of the capillary tube are connected to pressure transducers 67 and 68. Movement of the tell-tale rod 51 connected to the piston 48 is detected by means of a slidewire displacement transducer (not shown).

In operation the fluid to be examined is introduced from reservoir 55 into the both ends of cylinder 40 and the capillary tube 47 and the associated conduits, stop valves 52, 57, 58, 63 and 64 being open, taking care to purge the system of air. Stop valves 52 and 63 are then closed and the fluid pumped by means of pump 59 into space 53 of the cylinder 40 to move the piston 48 to within a short distance from the closure piece 42. Stop valve 64 is closed and pumping is stopped when the system has reached the desired pressure. The piston will now be in force equilibrium so that the pressure in space 53 is higher than the pressure in space 54 by an amount which is determined by the relative surface areas of the piston faces 49 and 50. The apparatus is then ready for the viscosity measurement to commence.

Stop valve 52 is opened allowing the fluid to pass from space 53 of the piston to space 54 via the capillary tube 47. The displacement of the tell-tale rod and the change in pressure across the capillary are measured by means of the transducers. These values together with their rate of change are recorded automatically by means not shown. The values obtained give a measure of the flow characteristics of the fluid and can be used to give a value for viscosity according to the well known Poiseuille equation, $$\eta = \frac{\pi r^4}{8L} \cdot \frac{\Delta P}{Q} t$$

where $\eta$ is the viscosity of a liquid, $\Delta P$ is the difference in pressure between the two ends of the tube of the length L and internal radius $r$ and Q is the volume of liquid which passes in time $t$. Because the viscosity of some liquids is very strongly dependent on the pressure applied this equation can give an inaccurate answer if the pressure difference across the capillary is large. However, by a suitable choice of capillary and dimensions of the cross-sectional areas of the piston and tell-tale rod the pressure difference can be maintained below 100 kg/cm² and the error introduced in ignoring the change of viscosity with pressure is then very small. When the pressure difference across the capillary exceeds 100 kg/cm² the change in viscosity with pressure may be taken account of by using a modified form of the Poiseuille equation.

The effect of temperature, as well as pressure, on the viscosity of the fluid can be measured by controlling the temperature of the fluid passing through the capillary by means of the bath 66. For measurements at high temperatures the bath may be replaced by an oven.

The apparatus described with reference to FIG. 2 may also be used to provide a measure of the compressibility of a fluid. This is accomplished by filling the system completely with fluid at atmospheric pressure with the piston fully withdrawn, that is with the side of the piston attached to the tell-tale rod contacting the end of the cylinder. Fluid is then pumped in through access port 43 and the liquid becomes compressed as the fluid pressure increases. The change in volume of the liquid originally contained in space 54 of the compressor and the associated connecting pipe-work can be determined by measuring the displacement of the tell-tale rod. The change in volume with change in pressure thus gives a measure of the compressibility of the fluid at a known temperature.

As a further example of the wide utility of the transfer compressor it may be used in providing a sealing pressure of lubricant in a rotary shaft clearance seal when used for example for preventing the fluid contents of a vessel maintained at high pressure from leaking past a stirrer shaft entering the vessel.

In this embodiment of the invention there is provided a means for enabling the contents of a vessel maintained at high pressure to be agitated without leakage of pressure comprising a shaft to carry the agitation means, a sleeve surrounding the shaft to form a seal with the circumference of the shaft at both ends of the sleeve, means to seal the sleeve to the vessel wall at an aperture in the wall so that the shaft passes into the vessel and the space within the vessel is sealed from the space outside the vessel by means of the seal between the sleeve and the shaft, wherein fluid e.g. a sealing lubricant at a pressure in excess of the pressure in the vessel is introduced between the shaft and the sleeve at a point intermediate the two ends of the sleeve. The fluid may be introduced by means of a conduit leading to the interface between the shaft and the sleeve, or a gap between the shaft and the sleeve intermediate the sleeve ends, the conduit being connected to a transfer compressor as hereinbefore described via the space containing the tell-tale rod.

Figure 3:
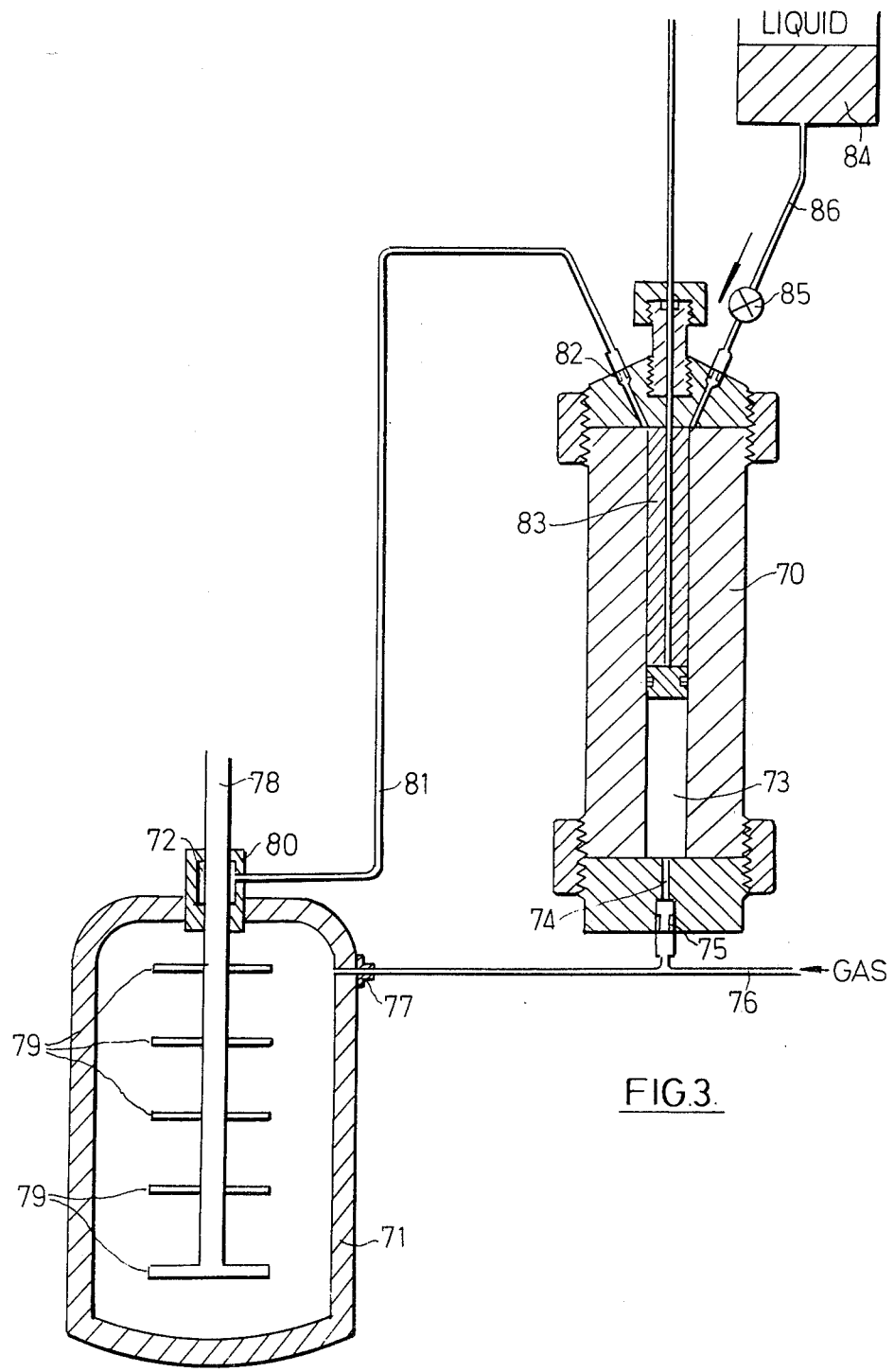
FIG. 3 is a sectional view of a transfer compressor when used with a sealing means for a high pressure vessel to provide a sealing pressure for the contents of the high pressure vessel.

This aspect of the invention is illustrated in FIG. 3. The assembly consists essentially of a transfer compressor 70, a high pressure vessel 71 and a sealing means 72. The sealing means is not shown in detail and may be any suitable type of seal, for example, the type known as a Morrison Seal which is described in the Proceedings of the Institute of Mechanical Engineers, Volume 170, page 697, 1959.

A space 73 of the transfer compressor is connected via a threaded connector 74 inserted in access port 75 into a gas supply line 76 supplying the high pressure vessel 71. The gas supply line 76 is connected to the vessel 71 through an access port 77. Vessel 71 is provided with an agitator shaft 78 fitted with paddles 79. Agitator shaft 78 passes slidably and rotatably through a gland 80 secured to the pressure vessel. The force on the end of the agitator shaft 78 inside the vessel 71 is opposed by some means, such as a thrust bearing, external to the vessel and not shown in the FIG. 3. Gland 80 is provided with a rotary sleeve seal 72 (not shown in detail) of the 'Morrison' type which is supplied with sealing fluid by means of supply line 81 leading from access port 82 of the compressor 70. Sealing fluid is supplied to space 83 on the tell-tale side of the compressor from a reservoir 84 through a non-return valve 85 in a supply line 86.

In operation gas is fed via supply line 76 to the vessel 71 via access port 77 and to the compressor via access port 75. A pressure greater than the gas pressure in the vessel is developed in the fluid on the tell-tale side of the compressor and is transmitted via line 81 to the rotary seal 72. The pressure applied to seal 72 is always greater than the pressure existing in vessel 71 the difference in pressure being determined by the pressure in the vessel and the relative cross-sectional areas of the piston and the tell-tale rod of the compressor.

Further uses of the transfer compressor described are for compressing fluids to very high pressures without requiring the complex moving seal arrangements which are normally required in such compressors or for pumping fluids which are difficult to handle or undesirable to introduce into primary high pressure equipment. Such fluids may be corrosive, of very high or very low viscosity, chemically unstable or having any property which could cause damage when introduced into complex equipment.

Accordingly there is further provided an apparatus for compressing or pumping fluids comprising a transfer compressor of the type described and a means for pressurising the fluid on the tell-tale side of the piston of the transfer compressor whereby a higher pressure developed in the fluid on the tell-tale side of the piston can be used to compress or pump a fluid in liquid or gaseous form contained on the opposite side of the piston.

Figure 4:
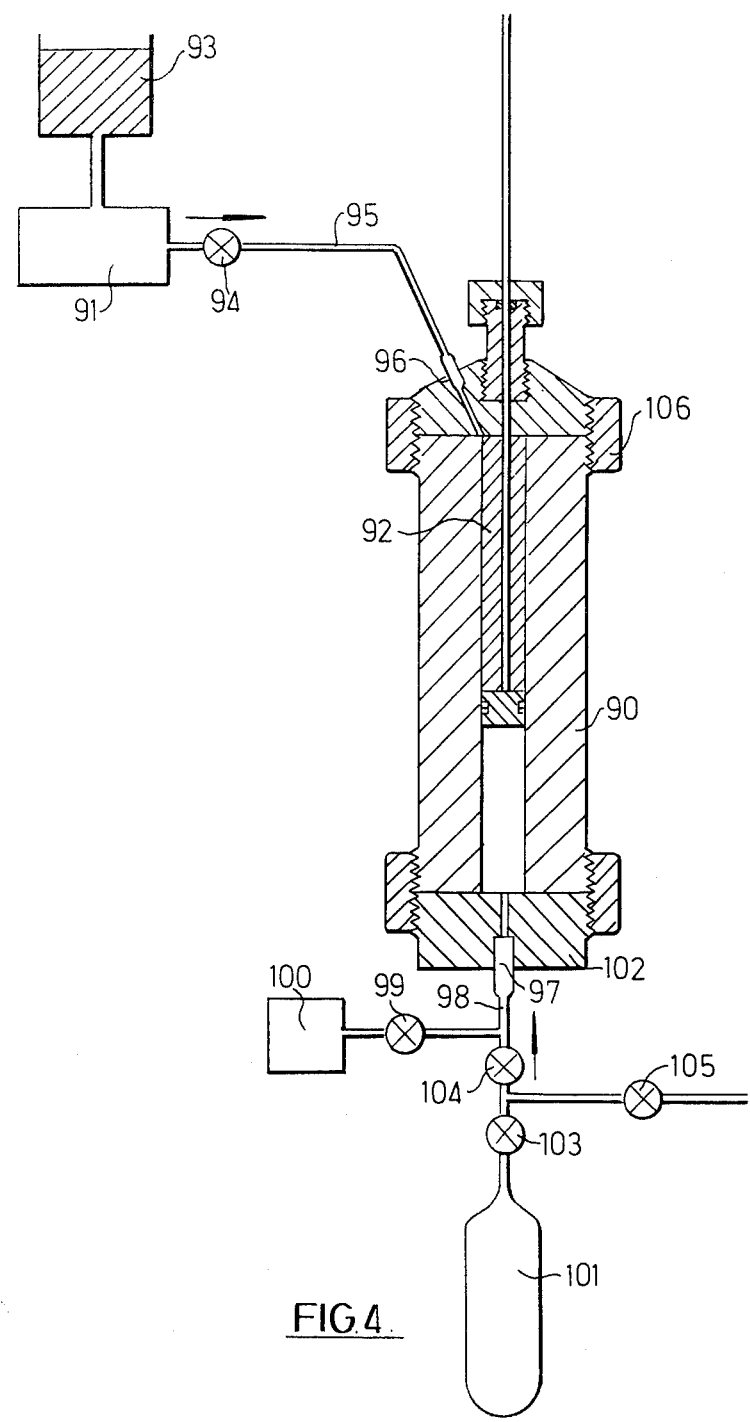
FIG. 4 is a sectional view of the transfer compressor when used together with an intensifier to provide a means for compressing fluids at high pressure.

This embodiment of the invention is now described with reference to FIG. 4 which shows the use of the transfer compressor together with an intensifier for providing a means for compressing a fluid to high pressure.

The apparatus consists essentially of a transfer compressor 90 connected to an air-operated intensifier 91 for pressurising fluid in the compressor. A space 92 on the tell-tale side of the compressor is supplied with fluid from reservoir 93 via non-return valve 94 in supply line 95 which in turn is connected to access port 96 of the compressor. Access port 97 on the opposite end 102 of the compressor is connected via supply line 98 provided with a valve 99 to a chamber 100 which can be pressurised with gas from a cylinder 101. Supply line 98 is further provided with a system of valves comprising a valve 103, a non-return valve 104 and a safety valve 105.

In operation gas from the cylinder 101 is introduced to the chamber 100 and via access port 97 into the end of the transfer compressor not containing the piston until the piston is contacting the end 106 of the compressor and the gas pressure in the system is the same as that in the supply cylinder 101. Stop valve 103 is then closed and fluid from reservoir 93 is pumped by means of the air-operated intensifier 91 via access port 96 to the transfer compressor to force the piston back towards end 102 of the compressor thereby compressing the gas contained in the compressor, the chamber 100 and the associated connecting lines. To achieve the maximum increase in pressure the volume of the specimen chamber and the connecting lines is kept to a minimum. An advantage of this method of compressing gases is that the pressure developed on the side of the piston not containing the tell-tale rod is always less than the pressure of the fluid on the other side of the piston by an amount which is dependent on the area of the piston occupied by the tell-tale rod. This prevents leakage of the gas into the fluid space. The area difference is preferably small in order that the pressure difference between the two sides of the piston is small and a very simple O-ring sealing means is sufficient to prevent a significant flow of fluid into the gas space.

The pressures obtainable by this device may be increased by the inclusion of suitable valve arrangements whereby repeated strokes of the transfer compressor produce increased pressures.

We claim:

1. A high pressure viscometer comprising: a transfer compressor for transmitting pressure from one fluid to another, said transfer compressor including a cylinder, a piston slidable within the cylinder, a space within the cylinder at each end of the piston, means for admitting fluid to each of the spaces, a tell-tale rod mounted on one end of the piston passing slidably and sealingly through an end of the cylinder, one end of the piston presenting a different area to the fluid in contact with it from the area presented by the other end of the piston to the fluid in contact with said other end, whereby the pressure exerted on the fluid at one end of the piston may be different from the pressure existing in the fluid at the other end of the piston; and a capillary tube having opposite ends connected to the spaces at the ends of the cylinder whereby a pressure difference generated between opposite ends of the piston by the application of pressure to the fluid contained in the end spaces of the cylinder causes the fluid to flow through the capillary at a rate which may be determined by the movement of the tell-tale rod.

2. A high pressure viscometer as in claim 1 in which the dimensions of the capillary, the piston and the tell-tale rod are such as to give a pressure difference across the capillary of less than 100 kg/cm$^2$.

3. A high pressure viscometer as in claim 1 in which the capillary tube is surrounded by a constant temperature vessel.

* * * * *